United States Patent [19]
Crowley et al.

[11] Patent Number: 5,280,044
[45] Date of Patent: Jan. 18, 1994

[54] FUNGICIDES

[75] Inventors: Patrick J. Crowley, Crowthorne; Alasdair T. Glen, Macclesfield; Rosamund A. Spence, Caversham, all of England

[73] Assignee: Imperial Chemical Industries PLC, London, England

[21] Appl. No.: 635,993

[22] Filed: Dec. 31, 1990

Related U.S. Application Data

[62] Division of Ser. No. 473,677, Feb. 2, 1990, Pat. No. 4,999,381.

Foreign Application Priority Data

Feb. 2, 1989 [GB] United Kingdom ............. 8902323
Oct. 17, 1989 [GB] United Kingdom ............. 8923366

[51] Int. Cl.$^5$ .................... A01N 37/18; C07C 233/65
[52] U.S. Cl. .................... 514/616; 514/210; 514/330; 514/123; 514/521; 514/618; 514/619; 564/152; 564/154; 564/155
[58] Field of Search ............. 564/155, 27, 51, 74, 564/152; 514/586, 599, 616, 597

[56] References Cited

U.S. PATENT DOCUMENTS

| | | | |
|---|---|---|---|
| 3,646,136 | 2/1972 | Hoegerle et al. | 564/51 |
| 4,060,638 | 11/1977 | Anderson | 564/155 |
| 4,485,105 | 11/1984 | Sheperd | 514/619 |
| 4,555,525 | 11/1985 | Lertora et al. | 514/616 |
| 4,623,662 | 11/1986 | DeVries | 514/586 |
| 4,666,938 | 5/1987 | Takahashi et al. | 514/479 |
| 4,666,943 | 5/1987 | Noguchi et al. | 514/629 |
| 4,826,841 | 5/1989 | Gajewski | 514/237.5 |

FOREIGN PATENT DOCUMENTS

| | | | |
|---|---|---|---|
| 0758433 | 5/1971 | Belgium | 564/27 |
| 0381330 | 8/1990 | European Pat. Off. | 564/155 |
| 1168918 | 8/1961 | Fed. Rep. of Germany | 564/155 |
| 3822448 | 3/1990 | Fed. Rep. of Germany | 564/51 |
| 0080351 | 5/1982 | Japan | 514/619 |
| 0067657 | 4/1983 | Japan | 564/155 |
| 0950714 | 2/1964 | United Kingdom | 564/155 |

OTHER PUBLICATIONS

Ito, Y. et al., "p-Aminosalicylic Acid Derivatives", CA 105, 97176j (1986).
Sasse, J. et al., "Preparation of 2-halo-4-ureidobenzamides as herbicides", CA 113, 97210f (1990)-[abstract of reference M above].
Patent Abstract of Japan, vol. 6, No. 40 (C-94)(918) Mar. 12, 1982.

*Primary Examiner*—Glennon H. Hollrah
*Assistant Examiner*—Shailendra Kumar
*Attorney, Agent, or Firm*—Cushman, Darby & Cushman

[57] ABSTRACT

Fungicidal compounds of the formula (I):

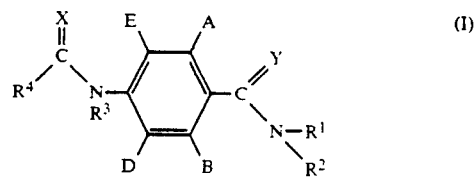

in which A and B are independently H, fluoro, chloro, bromo, $C_{1-4}$ alkyl, $C_{1-4}$ alkoxy or halo($C_{1-4}$)alkyl provided that both are not H; D and E are independently H or fluoro; $R^1$ is H, $C_{1-4}$ alkyl or $C_{1-4}$ alkoxy; $R^2$ is $CC_{1-4}$ alkyl, $C_{1-4}$ alkoxy or optionally substituted phenyl, or $R^1$ and $R^2$ together with the nitrogen atom to which they are attached join to form a morpholine, piperidine, pyrrolidine or azetidine ring which is optionally substituted with $C_{1-4}$ alkyl; $R^3$ is H; $R^4$ is trichloromethyl, $C_{2-8}$ alkyl (optionally substituted with halogen, $C_{1-8}$ alkoxy or R'S(O) in which R' is $C_{1-4}$ alkyl, $C_{2-4}$ alkenyl or $C_{2-4}$ alkynyl and n is 0, 1 or 2), cyclopropyl (optionally substituted with halogen or $C_{1-4}$ alkyl), $C_{2-8}$ alkenyl, $C_{2-8}$ alkynyl, $C_{1-8}$ alkoxy, mono- or di($C_{1-4}$)alkyl-amino or the group, R"ON=C(CN) in which R" is $C_{1-4}$ alkyl, or $R^3$ and $R^4$ together with the group C(O)N to which they are attached join to form an azetidin-2-one ring which is optionally substituted with halogen or $C_{1-4}$ alkyl; and X and Y are independently oxygen or sulphur.

10 Claims, No Drawings

FUNGICIDES

This is a division of application Ser. No. 07/473,677, filed Feb. 2, 1990, U.S. Pat. No. 4,999,381.

This invention relates to novel fungicidal acylaminobenzamides, to processes for preparing them, to fungicidal compositions containing them and to methods of using them to combat fungi, especially fungal infections of plants.

Acknowledgement is made of UK Application No. 42454/77 from which U.S. Pat. No. 4282218, for example, claims priority and of EP-A-0127990. The former describes acylanilides which have antiandrogenic properties and the latter describes aniline derivatives which have fungicidal properties.

According to the present invention there is provided a compound of the formula (I):

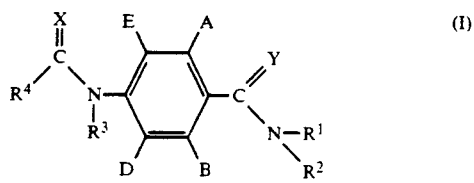
(I)

in which A and B are independently H, fluoro, chloro, bromo, $C_{1-4}$ alkyl, $C_{1-4}$ alkoxy or halo($C_{1-4}$)alkyl provided that both are not H; D and E are independently H or fluoro; $R^1$ is H, $C_{1-4}$ alkyl or $C_{1-4}$ alkoxy; $R^2$ is $C_{1-4}$ alkyl, $C_{1-4}$ alkoxy or optionally substituted phenyl, or $R^1$ and $R^2$ together with the nitrogen atom to which they are attached join to form a morpholine, piperidine, pyrrolidine or azetidine ring which is optionally substituted with $C_{1-4}$ alkyl; $R^3$ is H; $R^4$ is trichloromethyl, $C_{2-8}$ alkyl (optionally substituted with halogen, $C_{1-8}$ alkoxy or $R'S(O)_n$ in which $R'$ is $C_{1-4}$ alkyl, $C_{2-4}$ alkenyl or $C_{2-4}$ alkynyl and n is 0, 1 or 2), cyclopropyl (optionally substituted with halogen or $C_{1-4}$ alkyl), $C_{2-8}$ alkenyl, $C_{2-8}$ alkynyl, $C_{2-8}$ alkoxy, mono- or di($C_{1-4}$)- alkylamino or the group, $R''ON=C(CN)$ in which $R''$ is $C_{1-4}$ alkyl, or $R^3$ and $R^4$ together with the group C(O)N to which they are attached join to form an azetidin-2-one ring which is optionally substituted with halogen or $C_{1-4}$ alkyl; and x and Y are independently oxygen or sulphur.

Alkyl groups and the alkyl moiety of other alkyl-containing groups can be in the form of straight or branched chains. Examples are methyl, ethyl, propyl (n-and iso-propyl), butyl (n-, sec, iso- and t-butyl), 1,1-dimethylpropyl and 1,1-dimethylbutyl. Alkenyl and alkynyl groups can also be in the form of straight or branched chains. Examples are 1,1-dimethylbut-3-enyl and 1,1-dimethylprop-2-ynyl.

Halogen includes fluorine, chlorine and bromine.

Optional substituents of phenyl include: halogen, $C_{1-4}$ alkyl (for example, methyl), $C_{1-4}$ alkoxy (for example methoxy), $C_{1-4}$ alkylthio (for example methylthio), trifluoromethyl, trifluoromethoxy, nitro, cyano, $C_{1-4}$ alkoxycarbonyl, amino and mono- and di($C_{1-4}$)alkylamino.

In one aspect the invention provides a compound of formula (I) in which A and B are independently H, fluoro, chloro or bromo provided that both are not H; D and E are both H; $R^1$ is hydrogen or $C_{1-4}$ alkyl; $R^2$ is $C_{1-4}$ alkyl, $C_{1-4}$ alkoxy or phenyl, or $R^1$ and $R^2$ together with the nitrogen atom to which they are attached join to form a morpholine, piperidine, pyrrolidine or azetidine ring; $R^3$ is hydrogen; $R^4$ is $C_{3-6}$ alkyl (optionally substituted with halogen, methoxy, methylthio or methylsulphonyl), cyclopropyl (optionally substituted with methyl), $C_{3-6}$ alkenyl, $C_{3-6}$ alkynyl, $C_{1-4}$ alkoxy or the group $CH_3ON=C(CN)$; and X and Y are both oxygen.

In another aspect the invention provides a compound of formula (I) in which A is chloro; B, D and E are all H; $R^1$ is hydrogen, methyl or ethyl; $R^2$ is methyl, ethyl or phenyl, or $R^1$ and $R^2$ together with the nitrogen atom to which they are attached join to form a morpholine or piperidine ring; $R^3$ is hydrogen; $R^4$ is $C_{3-4}$ alkyl (for example iso-propyl or t-butyl) or cyclopropyl; and X and Y are both oxygen.

In yet another aspect the invention provides a compound of formula (I) in which A is chloro; B, D and E are all H; $R^1$ and $R^2$ are independently methyl or ethyl (but suitably both methyl or both ethyl) or together with the nitrogen atom to which they are attached join to form a morpholine or piperidine ring; $R^3$ is hydrogen; $R^4$ is iso-propyl, t-butyl or cyclopropyl; and X and Y are both oxygen.

In yet another aspect the invention provides a compound of the formula (I.1):

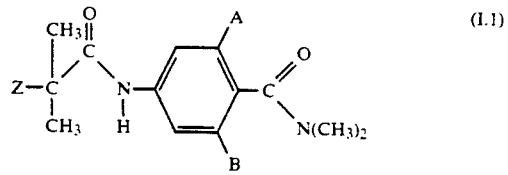
(I.1)

in which A and B are independently chloro, bromo or methyl or B is H; and z is fluoro, chloro, bromo, methyl, ethyl or methoxy. Amongst these compounds are to be noted those in which B is H and those in which A and B are both chloro or both methyl. Compounds of particular interest are those in which A is chloro; B is H; and Z has any of the meanings given above; and also those in which A is chloro or bromo; B is H, or A and B are both chloro; and Z is methyl.

The invention is illustrated by the compounds listed in Tables I, II and III which follow.

TABLE I

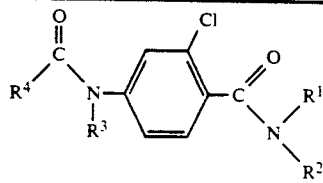

| Compound No. | $R^1$ | $R^4$ | $R^3$ | $R^4$ | mpt (°C.) |
|---|---|---|---|---|---|
| 1 | $CH_3$ | $CH_3$ | H | $(CH_3)_2CH$ | 182-184 |

TABLE I-continued

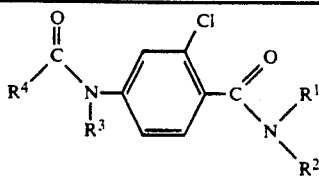

| Compound No. | R¹ | R⁴ | R³ | R⁴ | mpt (°C.) |
|---|---|---|---|---|---|
| 2 | $C_2H_5$ | $C_2H_5$ | H | $(CH_3)_2CH$ | 154–157 |
| 3 | —$(CH_2)_2$—O—$(CH_2)_2$— | | H | $(CH_3)_2CH$ | 180–182 |
| 4 | —$(CH_2)_5$— | | H | $(CH_3)_2CH$ | 182–184 |
| 5 | $CH_3$ | $CH_3$ | H | $(CH_3)_3C$ | 202–203 |
| 6 | $CH_3$ | $CH_3$ | H | ▷ | 179–180 |
| 7 | $C_2H_5$ | H | H | $(CH_3)_2CH$ | 189–190 |
| 8 | H | $C_6H_5$ | H | $(CH_3)_2CH$ | 223–224 |
| 9 | $CH_3$ | $CH_3$ | H | $Cl_3C$ | 185–186 |
| 10 | $CH_3$ | $CH_3$ | H | $ClCH_2(CH_3)_2C$ | 179–181 |
| 11* | $CH_3$ | $CH_3$ | —$CH_2$—$C(CH_3)_2$— | | 122–123 |
| 12 | $CH_3$ | $CH_3$ | H | $CH_3S(CH_3)CH$ | 158–161 |
| 13 | $CH_3$ | $CH_3$ | H | ▷–$CH_3$ | 155–156 |
| 14 | $CH_3$ | $CH_3$ | H | $CH_3CH_2(CH_3)_2C$ | 155–156 |
| 15 | $CH_3$ | $CH_3$ | H | $CH_3CH_2CH_2(CH_3)_2C$ | 125–126 |
| 16 | $CH_3$ | $CH_3$ | H | $Br(CH_3)_2C$ | 181.5–182 |
| 17 | $CH_3$ | $CH_3$ | H | $Cl(CH_3)_2C$ | 168–169 |
| 18 | $CH_3$ | $CH_3$ | H | $CH_2=CHCH_2(CH_3)_2C$ | 120–121.5 |
| 19 | $CH_3$ | $CH_3$ | H | $(Cl)_2CH(CH_3)_2C$ | 180–181 |
| 20 | $CH_3$ | $CH_3$ | H | $(CH_3)_3CO$ | 206–207 |
| 21 | $CH_3$ | $CH_3$ | H | $CH_3O(CH_3)_2C$ | 141–143 |
| 22 | $CH_3$ | $CH_3$ | H | $CH_3S(CH_3)_2C$ | 133.5–135 |
| 23 | $CH_3$ | $CH_3$ | H | $CH_3SO_2(CH_3)_2C$ | 169–170 |
| 24 | $CH_3$ | $CH_3$ | H | $(CH_3)_2N$ | 125–126 |
| 25 | $CH_3$ | $CH_3$ | H | $(CH_3)_3CCH_2$ | 194–195.5 |
| 26 | $CH_3$ | $CH_3$ | H | $HC\equiv C(CH_3)_2C$ | 179–181 |
| 27 | $CH_3$ | $CH_3$ | H | $BrCH_2(Br)_2C$ | 192.5–193.3 |
| 28 | $CH_3$ | $CH_3$ | H | $BrCH_2(Br)(CH_3)C$ | 190 |
| 29 | $CH_3$ | $CH_3CH_2$ | H | $(CH_3)_3C$ | 151–153 |
| 30 | $CH_3CH_2$ | $CH_3CH_2$ | H | $(CH_3)_3C$ | 161–163 |
| 31 | $CH_3$ | $(CH_3)_2CH$ | H | $(CH_3)_3C$ | 139–141 |
| 32 | —$(CH_2)_4$— | | H | $(CH_3)_3C$ | 173–174 |
| 33 | —$(CH_2)_3$— | | H | $(CH_3)_3C$ | 185–187 |
| 34 | $CH_3$ | $CH_3CH_2CH_2$ | H | $(CH_3)_3C$ | 175–176 |
| 35 | $CH_3$ | $CH_3O$ | H | $(CH_3)_3C$ | Oil |
| 36 | $CH_3$ | $CH_3$ | H | $(Cl)_2(CH_3)C$ | 154.5–156.5 |
| 37 | $CH_3$ | $CH_3$ | H | $CH_3ON=C(CN)$ | 128–129 |
| 38 | $CH_3$ | $CH_3$ | H | $F(CH_3)_2C$ | 125–128 |
| 39 | $CH_3$ | $CH_3$ | H | $CH_2=CH(CH_3)_2C$ | 137–139 |
| 40 | $CH_3$ | $CH_3$ | H | $CH_3OCH_2(CH_3)_2C$ | 101–103 |
| 41 | $CH_3$ | $CH_3$ | H | $CH_3SCH_2(CH_3)_2C$ | |
| 42 | $CH_3$ | $CH_3$ | H | $FCH_2(CH_3)_2C$ | 152–154 |
| 43 | $CH_3$ | $CH_3$ | H | $F_2CH(CH_3)_2C$ | |
| 44 | $CH_3$ | $CH_3$ | H | $CH_3CH=CH(CH_3)_2C$ | |
| 45 | $CH_3$ | $CH_3CH_2$ | H | $Cl(CH_3)_2C$ | 108–111 |
| 46 | $CH_3$ | $CH_3CH_2$ | H | $Br(CH_3)_2C$ | 133–135 |
| 47 | $CH_3$ | $CH_3CH_2$ | H | $F(CH_3)_2C$ | oil |
| 48 | $CH_3$ | $CH_3CH_2$ | H | $CH_3O(CH_3)_2C$ | 136–138 |
| 49 | $CH_3$ | $CH_3CH_2$ | H | $ClCH_2(CH_3)_2C$ | |
| 50 | $CH_3$ | $CH_3CH_2$ | H | $(CH_3)_2CH$ | |
| 51 | $CH_3$ | $CH_3CH_2$ | H | ▷–$CH_3$ | |
| 52 | $CH_3$ | $CH_3CH_2$ | H | $CH_3CH_2(CH_3)_2C$ | 130–132 |
| 53 | $CH_3$ | $CH_3CH_2$ | —$CH_2$—$C(CH_3)_2$— | | |
| 54 | $CH_3$ | $CH_3CH_2$ | H | $(CH_3)_2N$ | |
| 55 | $CH_3$ | $CH_3CH_2$ | H | $CH_2=CHCH_2(CH_3)_2C$ | |

TABLE I-continued

| Compound No. | R¹ | R² | R³ | R⁴ | mpt (°C.) |
|---|---|---|---|---|---|
| 56 | CH₃ | CH₃CH₂ | H | (CH₃)₃CO | |
| 57 | CH₃ | (CH₃)₂CH | H | Cl(CH₃)₂C | |
| 58 | CH₃ | (CH₃)₂CH | H | Br(CH₃)₂C | |
| 59 | CH₃ | (CH₃)₂CH | H | F(CH₃)₂C | |
| 60 | CH₃ | (CH₃)₂CH | H | CH₃O(CH₃)₂C | |
| 61 | CH₃ | (CH₃)₂CH | H | ClCH₂(CH₃)₂C | |
| 62 | CH₃ | (CH₃)₂CH | H | (CH₃)₂CH | |
| 63 | CH₃ | (CH₃)₂CH | H | cyclopropyl-CH₃ | |
| 64 | CH₃ | (CH₃)₂CH | H | CH₃CH₂(CH₃)₂C | |
| 65 | CH₃ | CH₃CH₂ | H | CH₂=CH(CH₃)₂C | 111–113 |
| 66 | CH₃ | CH₃ | H | HC≡CCH₂(CH₃)₂C | 154–155 |
| 67 | CH₃ | CH₃ | H | CH₃CH=CHCH₂(CH₃)₂C | 120 (dec.) |
| 68 | CH₃ | CH₃ | H | CH₂=CHCH₂CH₂(CH₃)₂C | 95–96 |

*Compound No 11 has the formula:

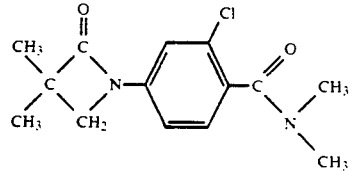

TABLE II

![structure]

| Compound | R¹ | R² | R³ | R⁴ | A | B | D | E | mpt (°C.) |
|---|---|---|---|---|---|---|---|---|---|
| 1 | CH₃ | CH₃ | H | (CH₃)₃C | CH₃O | H | H | H | 143–144 |
| 2 | CH₃ | CH₃ | H | (CH₃)₃C | CH₃ | H | H | H | 183–185 |
| 3 | CH₃ | CH₃ | H | (CH₃)₃C | Br | H | H | H | 219–222 |
| 4 | CH₃ | CH₃ | H | (CH₃)₃C | F | H | H | H | 125–130 |
| 5 | CH₃ | CH₃ | H | (CH₃)₃C | Cl | Cl | H | H | 187–188 |
| 6 | CH₃ | CH₃ | H | (CH₃)₃C | F | F | F | F | 187–189 |
| 7 | CH₃ | CH₃ | H | (CH₃)₃C | CF₃ | H | H | H | 198.7–199.6 |
| 8 | CH₃ | CH₃ | H | CH₃CH₂(CH₃)₂C | F | H | H | H | 110–113 |
| 9 | CH₃ | CH₃CH₂ | H | CH₃CH₂(CH₃)₂C | F | H | H | H | Gum |
| 10 | CH₃ | CH₃ | H | (CH₃)₃C | CH₃ | CH₃ | H | H | |
| 11 | CH₃ | CH₃ | H | (CH₃)₃C | F | F | H | H | |
| 12 | CH₃ | CH₃ | H | (CH₃)₃C | Cl | F | H | H | |
| 13 | CH₃ | CH₃ | H | (CH₃)₃C | CH₃ | F | H | H | |
| 14 | CH₃ | CH₃ | H | (CH₃)₃C | CH₃ | Cl | H | H | |
| 15 | CH₃ | CH₃ | H | (CH₃)₃C | Br | F | H | H | |
| 16 | CH₃ | CH₃ | H | (CH₃)₃C | Cl | Br | H | H | |
| 17 | CH₃ | CH₃ | H | (CH₃)₃C | Cl | H | F | H | |
| 18 | CH₃ | CH₃ | H | (CH₃)₃C | Cl | H | H | F | |
| 19 | CH₃ | CH₃ | H | (CH₃)₃C | Br | H | F | H | |
| 20 | CH₃ | CH₃ | H | (CH₃)₃C | CF₃ | F | H | H | |
| 21 | CH₃ | CH₃ | H | Cl(CH₃)₂C | Cl | Cl | H | H | |
| 22 | CH₃ | CH₃ | H | Br(CH₃)₂C | Cl | Cl | H | H | |
| 23 | CH₃ | CH₃ | H | F(CH₃)₂C | Cl | Cl | H | H | |
| 24 | CH₃ | CH₃ | H | CH₃O(CH₃)₂C | Cl | Cl | H | H | |
| 25 | CH₃ | CH₃ | H | CH₃CH₂(CH₃)₂C | Cl | Cl | H | H | |
| 26 | CH₃ | CH₃ | H | FCH₂(CH₃)₂C | Cl | Cl | H | H | |
| 27 | CH₃ | CH₃ | H | Cl(CH₃)₂C | Br | H | H | H | 188–189 |
| 28 | CH₃ | CH₃ | H | Br(CH₃)₂C | Br | H | H | H | 184.5–187 |
| 29 | CH₃ | CH₃ | H | F(CH₃)₂C | Br | H | H | H | 160–163 |
| 30 | CH₃ | CH₃ | H | CH₃O(CH₃)₂C | Br | H | H | H | 158–160 |
| 31 | CH₃ | CH₃ | H | CH₃CH₂(CH₃)₂C | Br | H | H | H | 159–161 |

TABLE II-continued

| Compound | R¹ | R² | R³ | R⁴ | A | B | D | E | mpt (°C.) |
|---|---|---|---|---|---|---|---|---|---|
| 32 | $CH_3$ | $CH_3$ | H | $ClCH_2(CH_3)_2C$ | Br | H | H | H | 186–188 |
| 33 | $CH_3$ | $CH_3$ | H | $FCH_2(CH_3)_2C$ | Br | H | H | H | |
| 34 | $CH_3$ | $CH_3$ | H | $Cl(CH_3)_2C$ | $CH_3$ | H | H | H | |
| 35 | $CH_3$ | $CH_3$ | H | $Br(CH_3)_2C$ | $CH_3$ | H | H | H | |
| 36 | $CH_3$ | $CH_3$ | H | $F(CH_3)_2C$ | $CH_3$ | H | H | H | |
| 37 | $CH_3$ | $CH_3$ | H | $CH_3O(CH_3)_2C$ | $CH_3$ | H | H | H | |
| 38 | $CH_3$ | $CH_3$ | H | $CH_3CH_2(CH_3)_2C$ | $CH_3$ | H | H | H | |
| 39 | $CH_3$ | $CH_3$ | H | $FCH_2(CH_3)_2C$ | $CH_3$ | H | H | H | |
| 40 | $CH_3$ | $CH_3$ | H | $CH_2{=}CH(CH_3)_2C$ | Br | H | H | H | |
| 41 | $CH_3$ | $CH_3$ | H | $CH_2{=}CH(CH_3)_2C$ | $CH_3$ | H | H | H | |
| 42 | $CH_3$ | $CH_3$ | H | $CH_2{=}CH(CH_3)_2C$ | Cl | Cl | H | H | |
| 43 | $CH_3$ | $CH_3CH_2$ | H | $(CH_3)_2CH$ | Cl | Cl | H | H | 149–150 |
| 44 | $CH_3$ | $CH_3CH_2$ | H | $(CH_3)_3C$ | Cl | Cl | H | H | 139–142 |
| 45 | $CH_3$ | $CH_3CH_2$ | H | $(CH_3)_3C$ | $CH_3$ | H | H | H | |
| 46 | $CH_3$ | $CH_3CH_2$ | H | $(CH_3)_3C$ | Br | H | H | H | 148–150 |
| 47 | $CH_3$ | $CH_3CH_2$ | H | $(CH_3)_3C$ | F | F | H | H | |
| 48 | $CH_3$ | $CH_3CH_2$ | H | $(CH_3)_3C$ | $CH_3$ | $CH_3$ | H | H | |
| 49 | $CH_3$ | $CH_3CH_2$ | H | $F(CH_3)_2C$ | Br | H | H | H | 97–100 |
| 50 | $CH_3$ | $CH_3CH_2$ | H | $F(CH_3)_2C$ | $CH_3$ | H | H | H | |
| 51 | $CH_3$ | $CH_3CH_2$ | H | $F(CH_3)_2C$ | Cl | Cl | H | H | |
| 52 | $CH_3$ | $CH_3CH_2$ | H | $F(CH_3)_2C$ | F | F | H | H | |
| 53 | $CH_3$ | $CH_3CH_2$ | H | $(CH_3)_2CH$ | Br | H | H | H | |
| 54 | $CH_3$ | $CH_3CH_2$ | H | $(CH_3)_2CH$ | $CH_3$ | H | H | H | |
| 55 | $CH_3$ | $CH_3CH_2$ | H | $(CH_3)_2CH$ | F | F | H | H | |
| 56 | $CH_3$ | $CH_3CH_2$ | H | $FCH_2(CH_3)_2C$ | Br | H | H | H | |
| 57 | $CH_3$ | $CH_3CH_2$ | H | $CH_3CH_2(CH_3)_2C$ | Br | H | H | H | 144–147 |
| 58 | $CH_3$ | $CH(CH_3)_2$ | H | $(CH_3)_3C$ | Br | H | H | H | |
| 59 | $CH_3$ | $CH(CH_3)_2$ | H | $(CH_3)_3C$ | $CH_3$ | H | H | H | |
| 60 | $CH_3$ | $CH(CH_3)_2$ | H | $F(CH_3)_2C$ | Br | H | H | H | |
| 61 | $CH_3$ | $CH(CH_3)_2$ | H | $FCH_2(CH_3)_2C$ | Cl | Cl | H | H | |
| 62 | $CH_3$ | $CH(CH_3)_2$ | H | $F(CH_3)_2C$ | $CH_3$ | H | H | H | |
| 63 | $CH_3$ | $CH_3CH_2$ | H | $Br(CH_3)_2C$ | Br | H | H | H | 108–110 |
| 64 | $CH_3$ | $CH_3CH_2$ | H | $Cl(CH_3)_2C$ | Br | H | H | H | 119–121 |
| 65 | $CH_3$ | $CH_3CH_2$ | H | $ClCH_2(CH_3)_2C$ | Br | H | H | H | 154–155 |
| 66 | $CH_3$ | $CH_3CH_2$ | H | $CH_3O(CH_3)_2C$ | Br | H | H | H | 133–134 |
| 67 | $CH_3$ | $CH(CH_3)_2$ | H | $CH_3O(CH_3)_2C$ | Br | H | H | H | Gum |
| 68 | $CH_3$ | $CH_3$ | 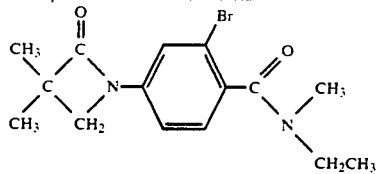 | | Br | H | H | H | 185–188 |
| 69* | $CH_3$ | $CH_3CH_2$ | $-CH_2-C(CH_3)_2-$ | | Br | H | H | H | Gum |

*Compound No 69 has the formula:

![Compound 69 structure]

TABLE III

![Table III structure]

| Compound | R¹ | R² | R⁴ | A | B | D | E | X | Y | mpt (°C.) |
|---|---|---|---|---|---|---|---|---|---|---|
| 1 | $CH_3$ | $CH_3$ | $(CH_3)_3C$ | Cl | H | H | H | O | S | 164–167 |
| 2 | $CH_3$ | $CH_3$ | $(CH_3)_3C$ | Cl | H | H | H | S | O | 120 (dec.) |
| 3 | $CH_3$ | $CH_3$ | $(CH_3)_3C$ | Cl | H | H | H | S | S | 154–156 |

The compounds of the invention can be made, for example, by the methods illustrated in Schemes 1 to 11.

Throughout these Schemes R¹, R², R⁴, A, B, D, and E are as defined before.

In Scheme 1, compounds of formula (II) can be prepared by reacting compounds of formula (VI) with an acid chloride $R^4COCl$ in a suitable organic solvent such as methylene chloride or toluene in the presence of a base such as a tertiary amine (for example triethylamine) or an alkali metal carbonate or hydroxide (for example sodium bicarbonate or sodium hydroxide).

Compounds of formula (VI) can be made by reduction of nitro compounds of formula (V) using standard methods known in the literature such as iron powder in aqueous ethanol.

Amides of formula (V) can be made from compounds of formula (III) by first converting a compound (III) into an acid chloride of formula (IV) by treatment with a standard reagent such as thionyl chloride or oxalyl chloride. The acid chloride (IV) is then reacted with an amine ($R^1R^2NH$ in a suitable organic solvent (such as methylene chloride or toluene) or in water, in the presence of a base (such as triethylamine or sodium bicarbonate or excess amine $R^1R^2NH$).

In Scheme 2, compounds of formula (II) can be prepared from compounds of formula (IX) by reaction with an amine $R^1R^2NH$ in a suitable organic solvent such as methylene chloride or tetrahydrofuran (THF) in the presence of a base such as triethylamine, sodium bicarbonate or excess $R^1R^2NH$.

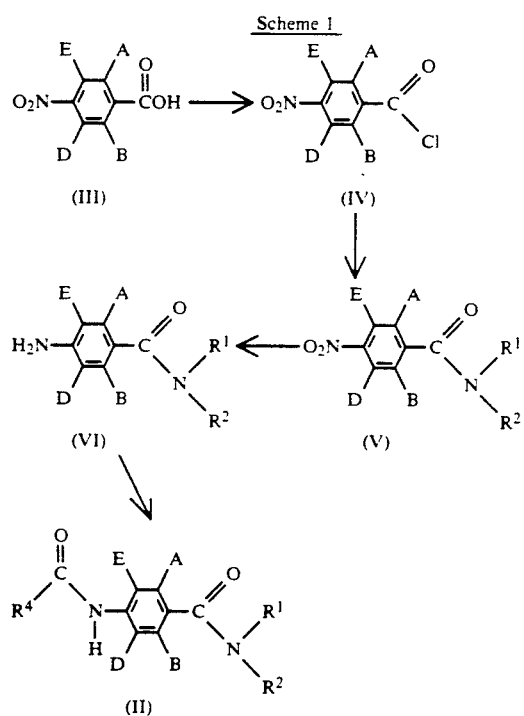

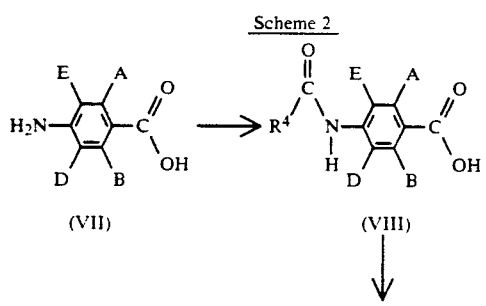

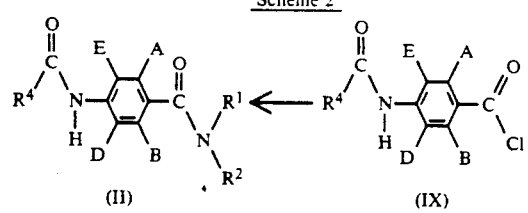

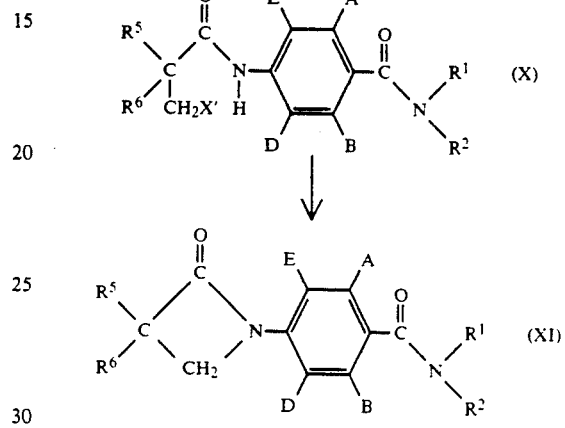

Acid chlorides of formula (IX) may be prepared from carboxylic acids of formula (VIII) by reaction with a standard reagent such as oxalyl chloride in a suitable dry solvent such as THF or methylene chloride and with a catalytic quantity of DMF being added if necessary.

Carboxylic acids of formula (VIII) may be prepared from the appropriately substituted 4-aminobenzoic acid (VII) by reaction with an acid chloride $R^4COCl$ in water in the presence of at least two equivalents of a base such as an alkali metal carbonate or hydroxide (for example sodium bicarbonate). The substituted 4-aminobenzoic acids (VII) can generally be made by methods described in the literature.

In Scheme 3, compounds of formula (XI) in which $R^5$ and $R^6$ are hydrogen, $C_{1-4}$ alkyl or halogen, are prepared from compounds of formula (X), in which X, is chlorine, bromine or iodine, by treatment with a base such as an alkali metal hydroxide (for example sodium hydroxide) in a two-phase system consisting of an organic solvent, such as methylene chloride, and water, in the presence of a phase-transfer catalyst (for example tetrabutylammonium bromide).

In Scheme 4, intermediates of formula (VIII) can be made by hydrolysis of compounds of formula (XIV) by standard methods in the literature such as treatment with aqueous mineral acid (for example aqueous sulphuric acid), or with aqueous alkali (for example aqueous sodium hydroxide with or without a cosolvent such as ethanol) or by aqueous diazotisation (for example with sodium nitrite in aqueous sulphuric acid). Compounds of formula (XIV) can be made from compounds of formula (XIII) by hydrolysis using standard methods in the literature such as treatment with aqueous mineral acid (for example aqueous sulphuric acid) or aqueous alkali (for example aqueous sodium hydroxide with or without a cosolvent such as ethanol) or by treatment with aqueous alkaline peroxide (for example aqueous hydrogen peroxide) containing sodium hydroxide with or without a cosolvent such as ethanol). Compounds of formula (XIII) can be made from compounds of formula (XII) by reaction with an acid chloride R⁴COCl in a suitable organic solvent (for example methylene chloride or toluene) in the presence of a base such as a tertiary amine (for example triethylamine) or an alkali metal carbonate or hydroxide (for example sodium bicarbonate or sodium hydroxide).

hydride or lithium diisopropylamide) in an inert organic solvent (for example tetrahydrofuran or dimethoxyethane) and then treated with an acid chloride R⁴COCl. Two equivalents of strong base may be needed for satisfactory yields. Compounds of general formula (XV) can be made from compounds of general formula (VII) by reaction with an alkanol R⁷OH, where R⁷ is $C_{1-4}$ alkyl, in the presence of an acid catalyst (for example concentrated sulphuric acid or hydrogen chloride gas).

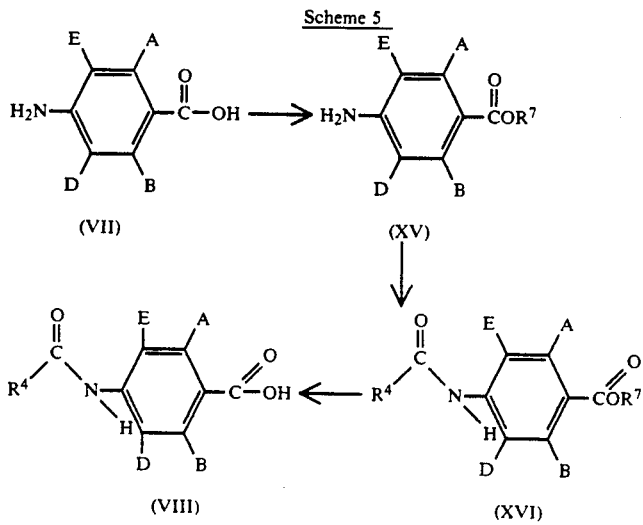

In Scheme 6, compounds of general formula (XVIII) where $R^8$ and $R^9$ are independently H, $C_{1-4}$ alkyl or $C_{1-4}$ haloalkyl, can be made by treatment of compounds of formula (XVII) with a fluoride transfer reagent (for example silver tetrafluoroborate) in a suitable solvent (for example acetonitrile).

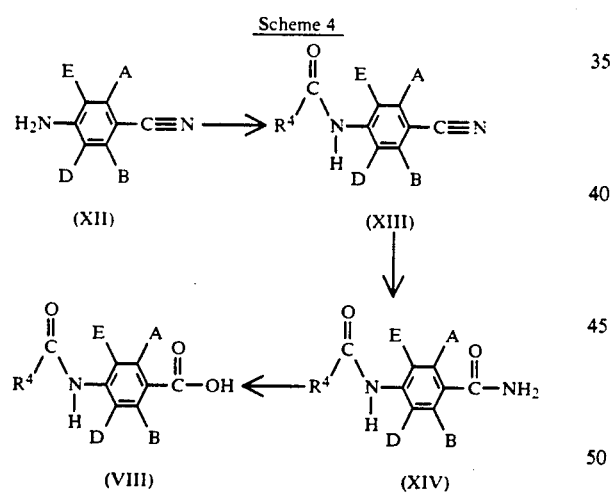

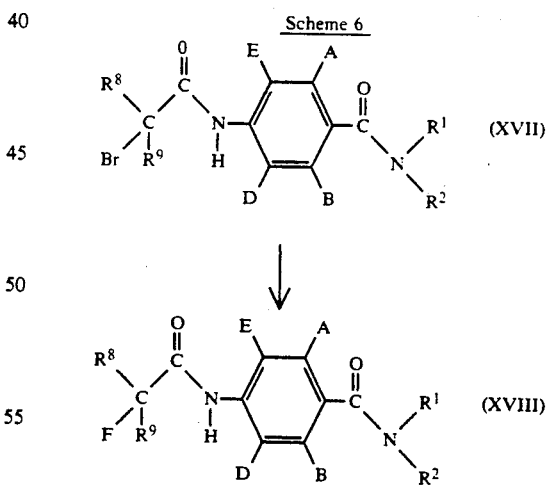

In Scheme 5, intermediates of general formula (VIII) can be made by hydrolysis of an ester (XVI) where $R^7$ is $C_{1-4}$ alkyl, with an alkali metal hydroxide (for example sodium hydroxide) in a suitable solvent such as water or ethanol or mixtures thereof. The ester of general formula (XVI) can be made from an aminobenzoic acid ester of general formula (xv) by several routes. Firstly by reaction with an acid chloride R⁴COCl in a suitable organic solvent (for example methylene chloride or toluene) in the presence of a base such as a tertiary amine (for example triethylamine) or an alkali metal carbonate or hydroxide (for example sodium bicarbonate or sodium hydroxide). Alternatively, when any of the substituents A, B, D and E are strongly electron-withdrawing the amino ester (XV) can be deprotonated with a strong base (for example sodium In Scheme 7 compounds of general formula (XX), where $R^8$ and $R^9$ are as defined for scheme 6, can be made from hydroxy compounds of general formula (XIX) by treatment with a fluorinating agent, (for example diethylaminosulphur trifluoride) in a suitable solvent (for example methylene chloride). Compounds of general formula (xx) can also be made by reaction of compounds of general formula (VI) with acid chlorides of general formula (XXXV), in a suitable solvent (such as methylene chloride or ethyl acetate) in the presence of a base (such as triethylamine or potassium carbonate).

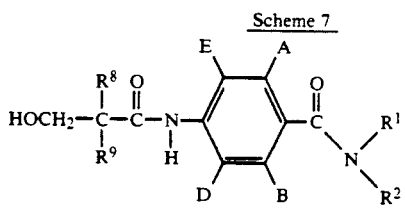

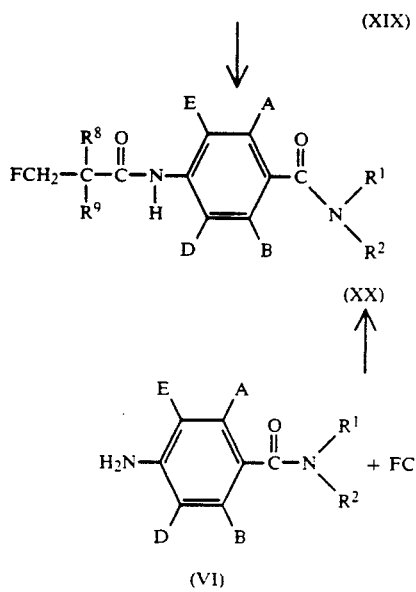

In Scheme 8 compounds of general formula (XXI) and (XXII) can be made by treatment of compounds of general formula (II) with a thionation reagent (for example phosphorus pentasulphide or Lawesson's reagent) in a suitable solvent (for example toluene or acetonitrile). Compounds (XXI) and (XXII) can either be produced together as a mixture, which can be separated by chromatography or crystallisation, or compound (XXI) can be produced alone, and can subsequently be converted to (XXII).

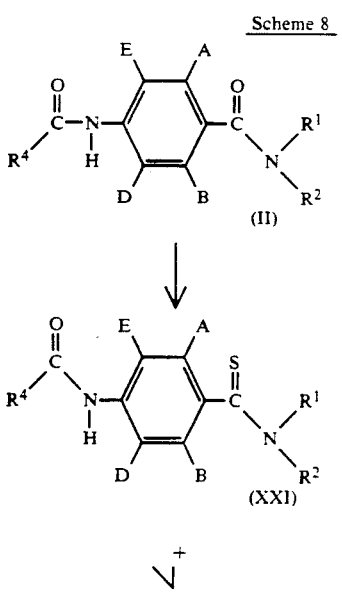

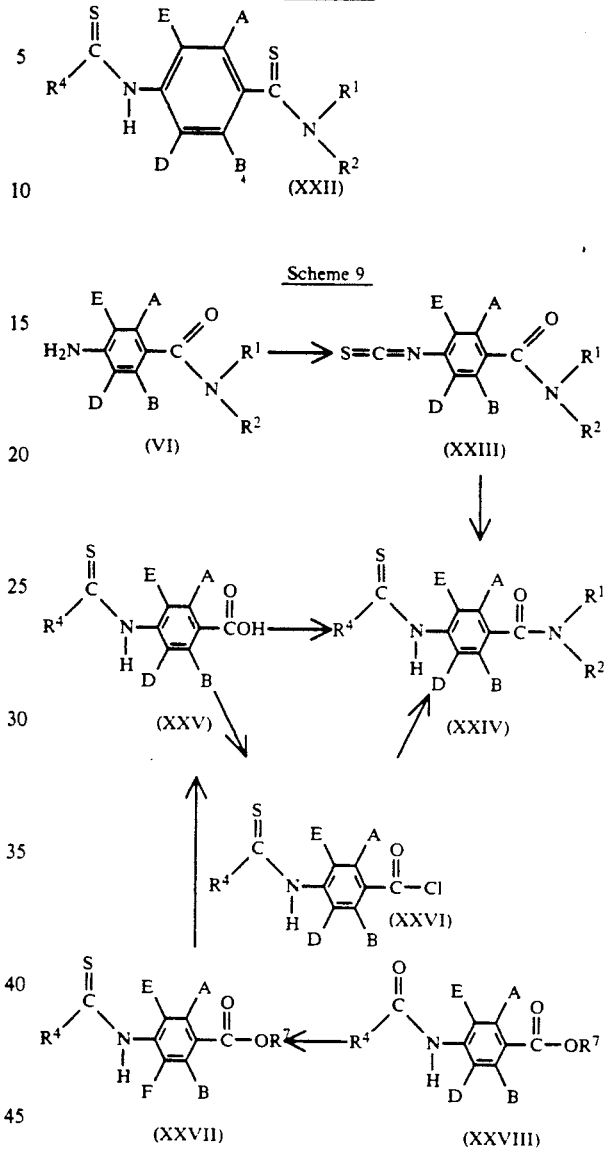

In Scheme 9 compounds of general formula (XXIV) may be made by reaction of isothiocyanates of general formula (XXIII) with organometallic reagents of type $R^4Li$, or $R^4Mghal$, where hal is a halogen such as chlorine or bromine, in a suitable solvent (such as tetrahydrofuran) at a temperature between $-78°$ C. and $+25°$ C.

Isothiocyanates of general formula (XXIII) can be made from compounds of general formula (VI) by standard methods, for example by treatment of compounds of general formula (VI) with thiophosgene.

Compounds of general formula (XXIV) can also be made from compounds of general formula (Xxv) by standard methods for making amides. For example (XXV) can be converted to an acid chloride of general formula (XXVI) by treatment with chlorination reagents (for example oxalyl chloride or thionyl chloride), and the acid chloride (XXVI) can be reacted with an amine $R^1R^2NH$ in the presence of a base (for example triethylamine or potassium carbonate). The carboxylic acids of general formula (XXV) can be made from the esters of general formula (XXVII) by hydrolysis using standard methods, (for example sodium hydroxide in methanol). The esters (XXVII) can in turn be made from compounds of general formula (XXVIII) by reaction with a thionation reagent (for example phosphorus pentasulphide or Lawesson's reagent) in a suitable solvent (for example toluene or acetonitrile).

In Scheme 10 compounds of general formula (XXXII), where $R^{11}$ is $C_{1-4}$ alkyl, can be made from compounds of general formula (XIX) by reaction with a halide $R^{11}$- hal, where hal is chlorine, bromine or iodine, in the presence of a base such as an alkali metal carbonate or oxide or hydroxide (for example barium oxide) in a suitable solvent (for example methanol). Compounds of general formula (XIX) can be made from compounds of general formula (XXXI) by hydrolysis with an alkali metal hydroxide (for example sodium hydroxide) in a suitable solvent (for example aqueous methanol). Compounds of general formula (XXXI)

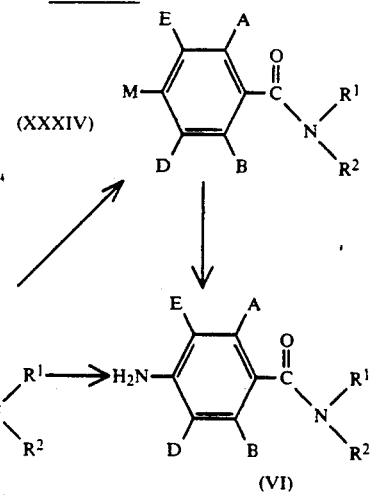

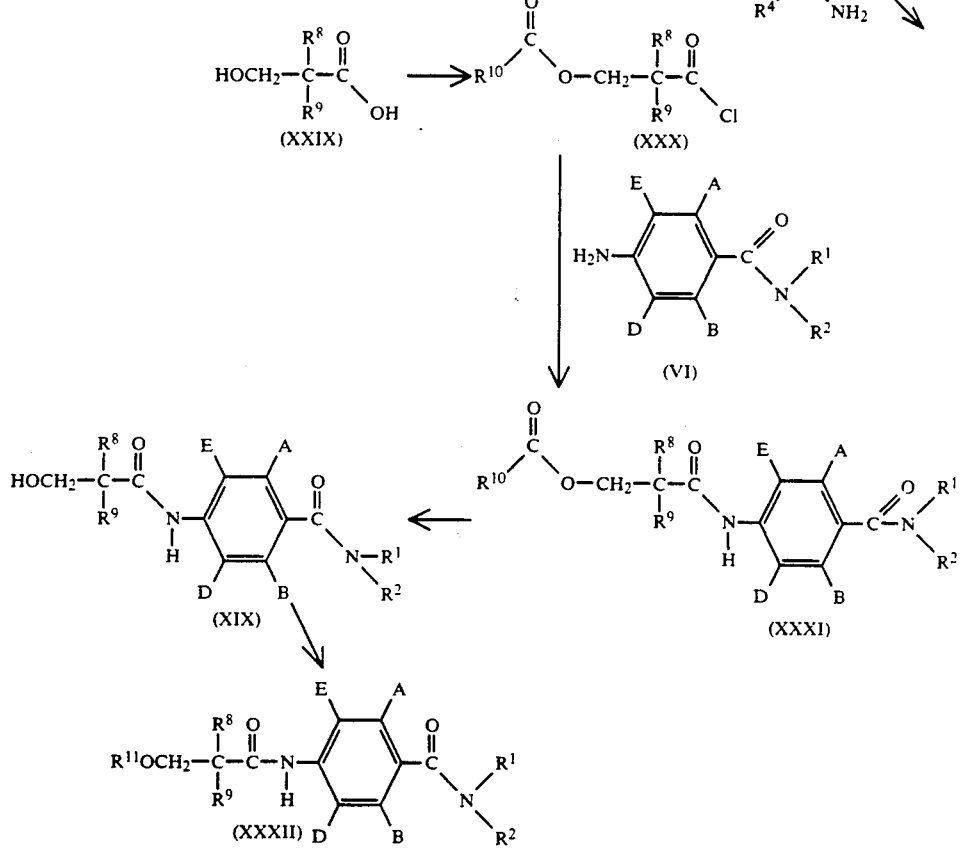

can be prepared from compounds of general formula (VI) by reaction with acid chlorides of general formula (XXX) in a suitable solvent (for example methylene chloride) in the presence of a base (for example triethylamine). Acid chlorides of general formula (XXX) can be made by treatment of hydroxy acids of general formula (XXXIX) with acid anhydrides of formula $(R^{10}CO)_2O$, followed by an acid chloride generating reagent (for example thionyl chloride or oxalyl chloride).

-continued
Scheme 11

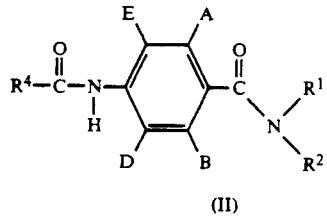

(II)

In Scheme 11 compounds of formula (II) can be prepared from compounds of formula (XXXIII), where L is a leaving group for example fluorine, chlorine, bromine, iodine, methanesulphonyloxy, p-toluenesulphonyloxy, or trifluoromethanesulphonyloxy, by reaction with a compound of general formula $R^4CO-NH_2$ and a base (for example sodium hydride, lithium diisopropylamide, alkali metal alkoxides or alkali metal carbonates). Compounds of formula (II) can also be made from anilines of general formula (VI) as described in Scheme 1. Anilines of general formula (VI) can be made by reaction of compounds of general formula (XXXIII) with ammonia in a suitable. solvent (for example ethanol or pyridine). Compounds of formula (VI) can also be made from compounds of general formula (XXXIV), where M is azido or hydrazino, by treatment with a reducing agent (for example hydrogen in the presence of a catalyst). Compounds of general formula (XXXIV) can be made from compounds of general formula (XXXIII) by reaction with alkali metal azides (for example sodium azide) or hydrazine, in suitable solvents (for example dimethylformamide or ethanol).

In a further aspect, the invention provides processes as herein described for preparing the compounds of the invention.

The compounds of the invention are active fungicides and may be used to control one or more of the following pathogens:

*Puccinis recondita* on wheat, *Erysiphe graminis* (powdery mildew) on barley, *Venturia inaegualis* (scab) on apples, *Cercospora arachidicola* on peanuts, *Plasmopara viticola* on vines and *Phytophthora infestans* on potatoes. In particular, they show notable activity against *Plasmopara viticola* and *Phytophthora infestans* as systemic treatments.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives. For example, certain mineral oil and natural plant oil (such as soya bean and rape seed oil) additives have been found to enhance several-fold foliar protectant activity against, for example, *Plasmopara viticola*.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropyl- naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are tetraconazole, (RS)-1-aminopropylphosphonic acid, (RS) (4-chlorophenyl)-2-phenyl-2-(1H-1,2,4-triazol-1-ylmethyl)butyronitrile, (RS)-4-chloro-N-(cyano(ethoxy)methyl)benzamide, (Z)-N-but-2-enyloxymethyl-2-chloro-2',6'-diethylacetanilide, 1-(2-cyano-2-methoxyiminoacetyl)-3-ethyl urea, 1-[(2RS,4RS;2RS,4RS)-4-bromo-2-(2,4-dichlorophenyl)tetrahydrofurfuryl)-1H-1,2,4-triazole, 3-(2,4-dichlorophenyl)-2-(1H-1,2,4-triazol-1-yl)quinazolin-4(3H)-one, 3-chloro-4-[4-methyl-2-(1H-1,2,4-triazol-1-methyl)-1,3-dioxolan-2-yl]phenyl-4-chlorophenyl ether, 4-bromo-2-cyano-N,N-dimethyl-6-trifluoromethylbenzimidazole-1-sulphonamide, 4-chlorobenzyl N-(2,4-dichlorophenyl)-2-(1H-1,2,4-triazol-1-yl)thioacetamidate, 5-ethyl-5,8-dihydro-8-oxo(1,3)-dioxolo(4,5-g)quinoline-7-carboxylic acid, α-[N-(3-chloro-2,6-xylyl)-2-methoxyacetamido)-γ-butyrolactone, anilazine, BAS 454, benalaxyl, benomyl, biloxazol, binapacryl, bitertanol, blasticidin S, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneamino-oxycarbonyl-)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, fluzilazole, folpet, fosetyl-aluminium, fuberidazole, furalaxyl, furconazole-cis, guazatine, hexaconazole, hydroxyisoxazole, imazalil, iprobenfos, iprodione, isoprothiolane, kasugamycin, mancozeb, maneb, mepronil, metalaxyl, methfuroxam, metsulfovax, myclobutanil, N-(4-methyl-6-prop-1-ynylpyrimidin-2-yl)-aniline, neoasozin, nickel dimethyldithiocarbamate, nitrothal-isopropyl, nuarimol, ofurace, organomercury compounds, oxadixyl, oxycarboxin, penconazole, pencycuron, pefurazoate, phenazin oxide, phthalide, polyoxen D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, techlofthalam, tecnazene, tebuconazole, thiabendazole, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention.

Throughout the Examples the term 'ether' refers to diethyl ether, magnesium sulphate was used to dry solutions and solutions were concentrated under reduced presaute. Reactions involving water-sensitive intermediates were performed under an atmosphere of nitrogen and solvents were dried before use, where appropriate. Where shown, infrared and NMR data are selective; no attempt is made to list every absorption in all cases. $^1$H NMR spectra were recorded using $CDCl_3$ solutions unless otherwise stated. The following abbreviations are used throughout:

| THF = tetrahydrofuran | s = singlet |
| DMF = N,N-dimethylformamide | d = doublet |
| NMR = nuclear magnetic resonance | t = triplet |
| IR = infrared | m = multiplet |
| m.p. = melting point | b = broad |

EXAMPLE 1

This example illustrates the preparation of 2-chloro-4-(2',2'-dimethylpropionamido)-N,N-dimethylbenzamide (compound No. 5 of Table-1).

Step 1

The preparation of 2-chloro-4-nitro-N,N-dimethylbenzamide.

2-chloro-4-nitrobenzoic acid (25.0 g) was refluxed in thionyl chloride (80 g) containing a few drops of DMF, for 3 hours. The excess thionyl chloride was then evaporated and the crude 2-chloro-4-nitrobenzoyl chloride added dropwise to 40% aqueous dimethylamine (70ml) at 0°-5° C. After strirring for 0.5 hour the yellow crystalline precipitate was filtered, washed with water and dried to give 2-chloro-4-nitro-N,N-dimethylbenzamide, as a pale yellow crystalline solid (24.97 g), m.p. 116°-117° C.

NMR ($CDCl_3$, 90 MHz) δ: 2.90(3H,s), 3.20(3H,s), 7.49(1H,d), 8.12(1H,d), 8.27(1H,m). IR (nujol mull): 3100, 1640 cm$^{-1}$.

Step 2

The preparation of 4-amino-2-chloro-N,N-dimethylbenzamide.

Iron powder (pre-reduced with hydrogen, 10.0 g) was suspended in ethanol (80ml) and water (10ml) and concentrated hydrochloric acid (4ml) were added with vigorous stirring. 2-Chloro-4-nitro-N,N-dimethylbenzamide (7.50 g) was added in small portions over 15 minutes and the mixture then heated to 50°-60° C. and stirred for 5 hours. The mixture was filtered through Celite and the ethanol evaporated. Water (200 ml) and concentrated hydrochloric acid (20 ml) were added and the reaction washed with ethyl acetate and then basified to pH8 with sodium bicarbonate and extracted with methylene chloride. The organic extract was dried and evaporated to give 4-amino-2-chloro-N,N-dimethylbenzamide as a grey crystalline solid (5.21 g) which was recrystallised from chloroform/ethyl acetate to give off-white crystals (3.46 g, m.p. 170° 173° C.).

NMR ($CDCl_3$, 270 MHz) δ: 2.89(3H,s), 3.11(3H,s), 3.87(2H,bs), 6.57(1H,dd), 6.67(1H,s), 7.07(1H,d). IR (liquid film): 3440-3340, 1640cm$^{-1}$.

Step 3

The preparation of 2-chloro-4-(2',2'-dimethylpropionamido)-N,N-dimethylbenzamide.

4-Amino-2-chloro-N,N-dimethylbenzamide (1.0 g) and triethylamine (1.21 g) were dissolved in methylene chloride (20 ml) and the solution was cooled to 0°-5° C. 2,2-Dimethylpropionyl chloride (1.21 g) was added dropwise keeping the temperature below 100° C. and the resulting orange solution stirred at 0°-10° C. for 0.5 hour. The organic solution was then washed with aqueous sodium bicarbonate and then water, dried and evaporated to give an orange solid. This was recrystallised from 3:1 ethyl acetate:chloroform to give 2-chloro-(2',2'-dimethylpropionamido)-N,N-dimethylbenzamide as an off-white crystalline solid (1.027 g), m.p. 202°-203° C.

NMR ($CDCl_3$, 270 MHz) δ1.32(9H,s), 2.86(3H,s), 3.13(3H,s), 7.16(1H,d), 7.34(1H,d), 7.68(1H,s), 7.72(1H,bs). IR (nujol mull): 3340, 1690, 1630 cm$^{-1}$.

EXAMPLE 2

This example illustrates the preparation of 2-chloro-4-(2'-methylpropionamido)-N,N-diethylbenzamide (compound No. 1 of Table I).

Step 1

The preparation of 2-chloro-4-(2'-methylpropionamido)benzoic acid.

4-Amino-2-chlorobenzoic acid was stirred in water (60 ml) and 1,2-dimethoxyethane (25 ml) with sodium bicarbonate (5.04 g) and the brown suspension cooled to 0°-5° C. 2-Methylpropionyl chloride (4.26 g) was added dropwise over 10 minutes with vigorous stirring, and the mixture was then stirred at 0°-10° C. for 2 hours. The mixture was poured into 2M hydrochloric acid and the pale brown precipitate washed with water and filtered and dried to give 2-chloro-4-(2'-methylpropionamido)benzoic acid as a pale brown crystalline solid (6.30 g), m.p. 206°-209° C.

NMR (d$_6$-DMSO, 270 MHz) δ: 1.05(6H,d), 2.53(1H,septet), 7.51(1H,dd), 7.78(1H,d), 7.86(1H,s), 10.19(1H,s), 14–12 (1H, very bs). IR (nujol mull): 3320, 1705, 1670 cm$^{-1}$.

Step 2

The preparation of 2-chloro-4-(2'-methylpropionamido)-benzoyl chloride.

Oxalyl chloride (0.63 g) in dry THF (5 ml) was added dropwise over 5 minutes to a solution of 2-chloro-4-(2'-methylpropionamido)benzoic acid (1.0 g) in dry THF (5 ml) at room temperature. After completion of the addition, dry DMF (1 drop) was added causing vigorous effervescence and a slight temperature rise. After stirring for 4 hours and addition of a further drop of DMF, the THF was evaporated to yield 2-chloro-4-(2'-methylpropionamido)benzoyl chloride as a viscous brown gum which was used without further purification. IR (liquid film): 3320, 3260, 3160, 3070, 1780, 1710, 1680, cm$^{-1}$.

Step 3

The Preparation of 2-chloro-4-(2'-methylpropionamido)-N,N-diethylbenzamide.

The crude 2-chloro-4-(2'-methylpropionamido)benzoyl chloride from the preceding reaction in dry THF (10 ml) was added dropwise with stirring over 10–15 minutes to a solution of diethylamine (1.46 g) in dry THF (10 ml), at 0°–5° C. After stirring at 0°–10° C. the reaction mixture was stood overnight at room temperature, poured into cold water and extracted with ethyl acetate. This extract was dried and evaporated to give a viscous gum which crystallised slowly and was then recrystallised from ethyl acetate to give 2-chloro-4-(2'-methylpropionamido)-N,N-diethylbenzamide as white crystals (0.507 g).

NMR (CDCl$_3$, 270 MHz) δ: 1.04(3H,t), 1.21(6H,d), 1.26(3H,t), 2.58(1H,Septet), 3.15(2H,q), 3.39(1H,bm), 3.74(1H,bm), 7.04(1H,d), 7.30(1H,dd), 7.51(1H,s), 8.58(1H,bs). IR (nujol mull): 3300, 3250, 3165, 1685 cm$^{-1}$.

EXAMPLE 3

This example illustrates the preparation of 1-[3'-chloro-4'-(N,N-dimethylcarbamoyl)phenyl]-3,3-dimethylazetidin-2-one (compound No. 11 of Table I).

Step 1

The preparation of 2-chloro-4-(3'-chloro-2',2'-dimethylpropionamido)-N,N-dimethylbenzamide.

3-Chloro-2,2-dimethylpropionyl chloride (1.86 g) was added dropwise over 5 minutes to 4-amino-2-chloro-N,N-dimethylbenzamide (2.00 g) suspended in dry methylene chloride (40 ml) and dry triethylamine (1.21 g) with stirring, keeping the temperature below 10° C. After stirring for 1 hour and warming to room temperature, methylene chloride (40 ml) was added and the solution washed with 2M hydrochloric acid, saturated aqueous sodium bicarbonate and then saturated brine. The solution was then dried and evaporated to yield a sticky yellow solid which was recrystallised from ethyl acetate/chloroform to give 2-chloro-4-(3'-chloro-2',2'-dimethylpropionamido)-N,N-dimethylbenzamide, as a white crystalline solid (2.349 g) m.p. 179°–181° C.

NMR (CDCl$_3$, 270 MHz) δ: 1.42(6H,s), 2.86(3H,s), 3.14(3H,s), 3.73(2H,s), 7.06(1H,d), 7.26(1H,dd), 7.50(1H,s), 8.48(1H,bs). IR (nujol mull): 3310, 1670, 1620 cm$^{-1}$.

Step 2

1-[3'-chloro-4'-(N,N-dimethylcarbamoyl)phenyl]-3,3-dimethylazetidin-2-one.

A solution of sodium hydroxide (4.00 g) and tetrabutylammonium bromide (0.10 g) in water (10 ml) was added to a suspension of 2-chloro-4-(3'-chloro-2',2'-dimethylpropionamido)-N,N-dimethylbenzamide (1.00 g) in methylene chloride (10 ml) and the two-phase system stirred at room temperature for 1 hour. Water (10 ml) and methylene chloride (10 ml) were then added and the whole methylene chloride layer washed with brine, dried and evaporated to give a pale yellow solid. This was recrystallised from ethyl acetate/hexane to give 1-[3'-chloro-4'-(N,N-dimethylcarbamoyl)phenyl]-3,3-dimethylazetidin-2-one as a white crystalline solid (0.516 g), m.p. 122°–123° C.

NMR (CDCl$_3$, 270 MHz) δ: 1.42(6H,s), 2.87(3H,s), 3.13(3H,s), 3.46(2H,s), 7.27(2H,t), 7.39(1H,s). IR (nujol mull): 3600–3100, 1740, 1625 cm$^{-1}$.

EXAMPLE 4

This example illustrate the preparation of 2-methoxy-4-(2',2'-dimethylpropionamido)-N,N-dimethylbenzamide (compound No. 1 of Table II).

Step 1

The preparation of methyl 2-methoxy-4-(2',2'-dimethylpropionamido)-benzoate.

Methyl 2-methoxy-4-aminobenzoate (3.03 g) and triethylamine (1.83 g) were stirred at 0°–5° C. in dry methylene chloride (50 ml). To this solution was added dropwise 2,2-dimethylpropionyl chloride (6.07 g) in dry methylene chloride (10 ml). After completion of the addition the mixture was stirred overnight at room temperature, and poured into dilute hydrochloric acid. The organic layer was separated and washed with dilute aqueous sodium bicarbonate and then water, and dried and evaporated to give an oil which crystallised. After heating with hexane the product was filtered as a white solid (3.61 g).

NMR (CDCl$_3$, 270 MHz) δ: 1.33(9H,s), 3.86(3H,s), 3.94(3H,s), 6.79(1H,dd), 7.45(1H,s), 7.79(1H,d), 7.82(1H,d).

Step 2

The preparation of 2-methoxy-4-(2',2'-dimethylpropionamido)-benzoic acid.

Methyl 2-methoxy-4-(2',2'-dimethylpropionamido)-benzoate (2.98 g) was stirred at room temperature with potassium hydroxide (0.725 g) in methanol (50 ml) for 3 hours, and then refluxed for 8 hours, and then poured into water. The mixture was extracted with ethyl acetate, and then acidified with hydrochloric acid. This acidified fraction was extracted with ethyl acetate and the extract was dried and evaporated to give the product as a solid (1.24 g).

NMR (CDCl$_3$, 270 MHz) δ: 1.36(9H,s), 4.10(3H,s), 6.78(1H,dd), 8.10(2H,m), 10.61(1H,s).

Step 3

The preparation of 2-methoxy-4-(2',2'-dimethylpropionamido)-benzoyl chloride.

To 2-methoxy-4-(2',2'-dimethylpropionamido)-benzoic acid (1.04 g) stirred in dry ether (25 ml) was added dropwise oxalyl chloride (1.4 g) in dry ether (5 ml) at room temperature, with a trace of DMF. After completion of the addition the mixture was stirred for 4 hours, and stood overnight. Some methylene chloride was added and the mixture evaporated to give the acid chloride as a yellow solid (1.12 g).

Step 4

Preparation of 2-methoxy-4-(2',2'-dimethylpropionamido)-N,N-dimethylbenzamide.

2-Methoxy-4-(2',2'-dimethylpropionamido)-benzoyl chloride (1.12 g) in dry THF (10 ml) was added dropwise over 30 minutes to a stirred solution of dimethylamine (1.17 g of a 40% aqueous solution) in THF (15 ml) at 0°-5° C. After completion of the addition the solution was stirred for 1 hour at 5°-10° C., stood at room temperature overnight, poured into water, and extracted with ethyl acetate. The extract was dried and evaporated to give the product as a yellow solid (0.889 g), m.p. 143°-144° C.

NMR (CDCl$_3$, 270 MHz) δ: 1.33(9H,s), 2.85(3H,s), 3.11(3H,s), 6.75(1H,dd), 7.15(1H,d), 7.48(1H,s), 7.65(1H,d).

EXAMPLE 5

This example illustrates the preparation of 2-trifluoromethyl-4-(2',2'-dimethylpropionamido)-N,N-dimethylbenzamide (compound No. 7 of Table II).

Step 1

The preparation of 2-trifluoromethyl-4-(2',2'-dimethylpropionamido)-benzonitrile.

2,2-Dimethylpropionyl chloride (3.79 g) in dry methylene chloride (5 ml) was added slowly dropwise to 4-cyano-3-trifluoromethylaniline (3.02 g) and triethylamine (3.34 g) in dry methylene chloride (50 ml) at 0°-5° C. After completion of the addition the mixture was stirred at room temperature for 1.5 hours, and then poured into dilute hydrochloric acid. The organic fraction was washed with dilute aqueous sodium bicarbonate, and water, and then dried and evaporated to give an orange solid. This was recrystallised to give the product as a yellow powder.

NMR (CDCl$_3$, 270 MHz) δ: 1.35(9H,s), 7.61(1H,s), 7.78(1H,d), 7.93(1H,dd), 8.03(1H,d).

Step 2

The preparation of 2-trifluoromethyl-4-(2',2'-dimethylpropionamido)-benzamide.

Hydrogen peroxide (85 ml of a 30% aqueous solution) and sodium hydroxide (8.5 ml of a 20% aqueous solution were added to 2-trifluoromethyl-4-(2',2'-dimethylpropionamido)-benzonitrile (5.03 g) in ethanol (140 ml), and the reaction mixture was stirred for 5 days at room temperature, during which time further ethanol (100 ml) was added. The reaction was then warmed at 50° C. for 24 hours, and was poured into water and extracted with ethyl acetate. The organic layer was then dried and evaporated to yield an oil which was flash chromatographed on silica to give the desired product (2.89 g).

NMR (CDCl$_3$, 270 MHz) δ: 1.35(9H,s), 5.80(2H,bs), 7.54(1H,s), 7.59(1H,d), 7.82(1H,dd), 7.90(1H,d).

Step 3

The preparation of 2-trifluoromethyl-4-(2',2'-dimethylpropionamido)-benzoic acid.

Concentrated hydrochloric acid (15 ml) was added to 2-trifluoromethyl-4-(2',2'-dimethylpropionamido)-benzamide (2.35 g) in glacial acetic acid (35 ml) at −5°−−0° C. A solution of sodium nitrite (1.807 g) in water (10 ml) was then added dropwise to the mixture and then was stirred for 1 hour at −5°−−0° C. After warming to room temperature the reaction was stirred for 24 hours, and was poured into water and extracted with methylene chloride. The methylene chloride fraction was washed with dilute aqueous sodium hydroxide, and the alkaline layer was acidified with dilute hydrochloric acid. The acidified layer was extracted with methylene chloride, and the organic layer was dried and evaporated to give the desired acid as a white solid, (0.926 g).

NMR (CDCl$_3$, 270 MHz) δ: 1.20(9H,s), 7.79(1H,d), 8.02(1H,dd), 8.19(1H,d), 9.69(1H,s).

Step 4

The preparation of 2-trifluoromethyl-4-(2',2'-dimethylpropionamido)-N,N-dimethylbenzamide.

Oxalyl chloride (0.64 g) in dry ether (7 ml) was added dropwise with stirring to 2-trifluoromethyl-4-(2',2'-dimethylpropionamido)-benzoic acid (0.926 g) in dry ether (40 ml) at room temperature. A drop of DMF was added during the addition. After two hours further oxalyl chloride (0.257 g) was added and the reaction stirred for a further two hours. The organic solution was then decanted from a precipitate, and evaporated to yield 2-trifluoromethyl-4-(2',2'-dimethylpropionamido)-benzoyl chloride as a liquid (1.136 g), which was used without purification.

The acid chloride (1.136 g) in dry THF (10 ml) was added dropwise with stirring over 30 minutes to dimethylamine (1.0 g of a 40% aqueous solution) in THF (15 ml) at 0°-5° C. The reaction was allowed to warm to room temperature and stood for 2½ days, and then poured into water, and extracted with ethyl acetate. The ethyl acetate fraction was washed with aqueous sodium bicarbonate, followed by dilute hydrochloric acid and then water. After being dried, the organic solution was evaporated to give 2-trifluoromethyl-4-(2',2'-dimethylpropionamido)-N,N-dimethylbenzamide, as a white solid (0.576 g), m.p. 198.7°-199.6° C.

NMR (CDCl$_3$, 270 MHz) δ: 1.35(9H,s), 2.80(3H,s), 3.12(3H,s), 7.22(1H,d), 7.72(1H,s), 7.75(1H,dd), 7.85(1H,d).

EXAMPLE 6

This example illustrates the preparation of 2,3,5,6-tetrafluoro-4-(2',2'-dimethylpropionamido)-N,N-dimethylbenzamide (compound No. 6 of Table II).

Step 1

The preparation of methyl 2,3,5,6-tetrafluoro-4-(2',2'-dimethylpropionamido)-benzoate.

Methyl 2,3,5,6-tetrafluoro-4-aminobenzoate (1.887 g) in dry THF (5 ml) was added to a suspension of sodium hydride (0.764 g of a 55% dispersion in oil) in dry THF (70 ml) stirred at room temperature. After completion of the effervescence, 2,2-dimethylpropionyl chloride (1.127 g) in dry THF (5 ml), was slowly added dropwise with cooling. The reaction was stirred at 10° C. for 1 hour and then poured into water, and extracted with ethyl acetate. The ethyl acetate fraction was washed with dilute hydrochloric acid and dilute aqueous sodium bicarbonate, dried and evaporated to give the product as a white solid, (2.44 g).

NMR (CDCl$_3$, 270 MHZ) δ: 1.36(9H,s), 3.97(3H,s), 7.05(1H,s).

Step 2

The preparation of 2,3,5,6-tetrafluoro-4-(2',2'-dimethylpropionamido)-benzoic acid.

Methyl 2,3,5,6-tetrafluoro-4-(2',2'-dimethylpropionamido)-benzoate (1.83 g), was stirred overnight with potassium hydroxide (0.669 g dissolved in the minimum quantity of water) in dimethoxyethane (DME) (60 ml), and was then poured into water. The mixture was extracted with ethyl acetate. The aqueous phase was acidified and extracted with ethyl acetate, and this ethyl acetate extract was dried and evaporated to give the acid as a pale yellow solid (1.538 g).

NMR (CDCl$_3$, 270 MHz) δ: 1.19(9H,s), 9.65(1H,s).

Step 3

The preparation of 2,3,5,6-tetrafluoro-4-(2',2'-dimethylpropionamido)-N,N-dimethylbenzamide.

Oxalyl chloride (1.00 g) in dry ether (5 ml) was added dropwise, with stirring to 2,3,5,6-tetrafluoro-4-(2',2'-dimethylpropionamido)-benzoic acid (1.47 g) in dry ether (35 ml), to which a drop of DMF had been added. After stirring for 2 hours at room temperature, the ether solution was decanted from insoluble material and evaporated to give the acid chloride as an oil (1.494 g), which was used without purification.

The acid chloride (1.494 g) in dry THF (10 ml) was slowly added dropwise over 30 minutes to dimethylamine (1.363 g) in THF (10 ml) at 0°–5° C. After stirring at 10° C. for 1.5 hours the reaction mixture was poured into water, and extracted with ethyl acetate. The extract was washed with aqueous sodium bicarbonate, and then dilute hydrochloric acid, dried and evaporated to give the product as a white powdery solid (1.279 g), m.p. 187°–189° C.

NMR (CDCl$_3$, 270 MHz) δ: 1.35(9H,s), 2.97(3H,s), 3.17(3H,s), 7.82(1H,s).

EXAMPLE 7

This example illustrates the preparation of 2-chloro-4-(2'-fluoro-2'-methylpropionamido)-N,N-dimethylbenzamide (compound No 38 of Table I).

Silver tetrafluoroborate (0.60 g) in acetonitrile (5 ml) was added to 2-chloro-4-(2'-bromo-2'-methylpropionamido)-N,N-dimethylbenzamide (1.065 g) in acetonitrile (150 ml) and the reaction mixture stirred under nitrogen, protected from light, for 6.5 hours. Ethyl acetate was added and the solution was filtered through celite and evaporated. The residue was dissolved in ethyl acetate again and filtered through celite and evaporated. The residue was purified by HPLC (eluent methylene chloride: acetonitrile, 2:1) to give the product as a white crystalline solid (0.319 g), m.p. 125°–128° C.

NMR (CDCl$_3$, 270 MHz) δ: 1.67(6H,d), 2.87(3H,s), 3.13(3H,s), 7.27(1H,d), 7.45(1H,dd), 7.80(1H,d), 8.18(1H,d).

EXAMPLE 8

This Example illustrates the preparation of 2-chloro-4-(3'-fluoro-2',2'-dimethylpropionamido)-N,N-dimethylbenzamide (compound 42 of Table I).

Step 1

The preparation of 2-chloro-4-(3'-acetoxy-2',2'-dimethylpropionamido)-N,N-dimethylbenzamide.

3-Acetoxy-2,2-dimethylpropionyl chloride (7.84 g) was added to a stirred solution of 4-amino-2-chloro-N,N-dimethylbenzamide (5.88 g) and triethylamine (5.99 g) in dry methylene chloride (15 ml) at 0°–5° C. After stirring for 30 minutes the reaction mixture was washed with dilute aqueous sodium bicarbonate, dilute sodium hydroxide, dilute hydrochloric acid, and then water. The organic layer was dried and evaporated to give an orange solid, which was triturated with hexane to give the desired product (9.08 g), m.p. 117°–120° C.

NMR (CDCl$_3$, 270 MHz) δ: 1.33(6H,s), 2.10(3H,s), 2.86(3H,s), 3.13(3H,s), 4.20(2H,s), 7.11(1H,d), 7.29(1H,dd), 7.60(1H,d), 8.21(1H,s).

IR (nujol mull) 1740, 1680, 1630 cm$^{-1}$

Step 2

The preparation of 2-chloro-4-(3'-hydroxy-2',2'-dimethylpropionamido)-N,N-dimethylbenzamide.

2-Chloro-4-(3'-acetoxy-2',2'-dimethylpropionamido)-N,N-dimethylbenzamide (8.14 g) was stirred in methanol (100 ml) containing potassium hydroxide (2.68 g) at room temperature for 2 hours. The methanol was evaporated and the residue extracted with ethyl acetate. The ethyl acetate was dried and evaporated to give the desired product, (5.03 g), m.p. 137°–139° C.

NMR (CDCl$_3$, 270 MHz) δ: 1.17(6H,s), 2.89(3H,s), 3.15(3H,s), 3.56(3H,d), 5.12(1H,t), 7.17(1H,d), 7.30(1H,dd), 7.69(1H,d), 9.49(1H,s).

Step 3

The preparation of 2-chloro-4-(3'-fluoro-2',2'-dimethylpropionamido)-N,N-dimethylbenzamide.

2-Chloro-4-(3'-hydroxy-2',2'-dimethylpropionamido)-N,N-dimethylbenzamide (1.008 g) in dry methylene chloride (40 ml), was added dropwise over 3 hours to a solution of diethylaminosulphur trifluoride (DAST) (0.68 g) in dry methylene chloride (20 ml) at −70° C. After ½ hour, a further amount of DAST (0.128 g) was added and the solution stirred at −70° C for ½ hour, and then warmed to room temperature overnight. The reaction mixture was washed with water, dried and evaporated to give a foam. This was triturated with hexane to give the desired product as a pale orange powder (0.269 g), m.p. 152°–4° C.

NMR (CDCl$_3$, 270 MHz) δ: 1.32(6H,d), 2.86(3H,s), 3.12(3H,s), 4.48(2H,d), 7.23(1H,d), 7.39(1H,dd), 7.75(1H,d), 7.77(1H,s).

EXAMPLE 9

This Example illustrates the preparation of 2-chloro-4-(3'-methoxy-2',2'-dimethylpropionamido)-N,N-dimethylbenzamide, (compound 40 of Table I).

Barium oxide (2.608 g) and barium hydroxide (0.540 g) were added to a solution of 2-chloro-4-(3'-hydroxy-2',2'-dimethylpropionamido)-N,N-dimethylbenzamide (0.510 g) in DMF (20 ml) at 0° C. After stirring at 0° C. for 15 minutes methyl iodide (3.64 g) was added dropwise. After allowing to warm to room temperature over 2 hours methylene chloride was added to the reaction and then the mixture was filtered through celite. The organic fraction was dried and evaporated to give a mobile liquid which was purified by HPLC (eluent: ethyl acetate) to give the desired product as a solid (0.101 g), m.p. 101°–103° C.

NMR (CDCl$_3$, 270 MHz) δ: 1.24(6H,s), 2.86(3H,s), 3.12(3H,s), 3.43(2H,s), 3.51(3H,s), 7.21(1H,d), 7.39(1H,dd), 7.75(1H,d), 9.05(1H,s).

EXAMPLE 10

This Example illustrates the preparation of 2-chloro-4-(2',2'-dimethyl-thiopropionamido)-N,N-dimethyl-thiobenzamide and 2-chloro-4-(2',2'-dimethylpropionamido)-N,N-dimethyl-thiobenzamide (compounds 3 and 1 respectively, of Table III).

2-Chloro-4-(2',2'-dimethylpropionamido)-N,N-dimethylbenzamide (1.00 g) was suspended in dry toluene (10 ml) and Lawesson's reagent (0.73 g) was added in small portions over 5 minutes, at room temperature. The suspension was refluxed for 1 hour, giving a clear solution, and the toluene was then evaporated to give a viscous gum, which was chromatographed on silica gel (eluent:methylene chloride) to give the two products:

1. 2-chloro-4-(2',2'-dimethyl-thiopropionamido)-N,N-dimethyl-thiobenzamide (0.104 g), m.p. 154°–156° C.

NMR (CDCl$_3$, 270 MHz) δ: 1.47(9H,s), 3.14(3H,s), 3.60(3H,s), 7.29(1H,d), 7.52(1H,dd), 7.82(1H,s), 8.85(1H,bs).

2. 2-chloro-4-(2',2'-dimethylpropionamido)-N,N-dimethyl-thiobenzamide (0.475 g), m.p. 164°–167° C.

NMR (CDCl$_3$, 270 MHz) δ: 1.31(9H,s), 3.11(3H,s), 3.58(3H,s), 7.25(1H,d), 7.33(1H,dd), 7.38(1H,bs), 7.74(1H,s).

EXAMPLE 11

This Example illustrates the preparation of 2-chloro-4-(2',2'-dimethyl-thiopropionamido)-N,N-dimethylbenzamide (compound 2 of Table 3).

Step 1

The preparation of 3-chloro-4-N,N-dimethylcarbamoylphenyl isothiocyanate.

Thiophosgene (1.15 g) was added dropwise over 3 minutes to sodium bicarbonate (1.68 g) suspended and stirred in water at room temperature. 4-Amino-2-chloro-N,N-dimethylbenzamide (1.00 g) was then added portionwise over 20 minutes, keeping the temperature at 20°–25° C. After a further 15 minutes the brown suspension was extracted with methylene chloride, and the organic layer dried and evaporated to give the desired product as an orange-yellow solid (1.18 g), which was used without further purification.

NMR (CDCl$_3$, 270 MHz) δ: 2.86(3H,s), 3.13(3H,s), 7.17(1H,dd), 7.26(1H,s), 7.28(1H,d).

IR (nujol mull): 2140–2080(bs), 1630 cm$^-$.

The preparation of 2-chloro-4-(2',2'-dimethyl-thiopropionamido)-N,N-dimethylbenzamide.

Tertiary-butyl lithium (3.2 ml of a 1.7M solution in pentane) was added over 20 minutes to a stirred solution of 3-chloro-4-N,N-dimethylcarbamoylphenyl isothiocyanate (1.17 g) in THF under nitrogen at −70° C. After stirring for 20 minutes at the same temperature water was carefully added followed by concentrated hydrochloric acid. The mixture was extracted with methylene chloride, which was then dried and evaporated to give a sticky brown solid (1.23 g). This was purified by HPLC (eluent:ethyl acetate) to give a yellow gum (0.099 g). Trituration with ether/toluene gave the desired product as a yellow solid, m.p. 120° C. (dec.).

NMR (CDCl$_3$, 270 MHz) δ: 1.66(9H,s), 2.88(3H,s), 3.14(3H,s), 7.25(1H,d), 7.45(1H,dd), 7.64(1H,d), 8.82(1H,bs).

EXAMPLE 12

This Example illustrates the preparation of 2-chloro-4-(2',2'-dimethylpent-4'-ynamido)-N,N-dimethylbenzamide (compound 66 of Table I).

Step 1

The preparation of ethyl 2,2-dimethylpent-4-ynoate.

Lithium diisopropylamide (13.7 ml of a 1.5M solution of the mono-THF complex in cyclohexane) was added dropwise over 20 minutes to a stirred solution of ethyl isobutyrate (2.38 g) in dry THF (10 ml) under nitrogen keeping the temperature below −60° C. After 1 hour propargyl bromide (2.45 g) in dry THF (5 ml) was added dropwise, keeping the temperature below −60° C. The reaction was allowed to warm to room temperature over 2 hours and was then poured into water and extracted with ethyl acetate. The ethyl acetate fraction was dried and evaporated to give an orange-brown liquid, which was distilled (Kugelrohr, 115° C./60mm) to give the desired product (1.39 g).

NMR (CDCl$_3$, 270 MHz) δ: 1.19(3H,t), 1.21(6H,s), 1.93(1H,t), 2.38(2H,d), 4.08(2H,q).

Step 2

The preparation of 2,2-dimethylpent-4-ynoic acid.

Ethyl 2,2-dimethylpent-4-ynoate (1.39 g) was stirred with potassium hydroxide (1.07 g) in methanol (20 ml) for 7½ hours at 40° C., and then stood overnight. The reaction was poured into water, and washed with ethyl acetate. The aqueous layer was acidified and extracted with ethyl acetate. This layer was then dried and evaporated to give the desired acid as a liquid (1.05 g).

NMR (CDCl$_3$, 270 MHz) δ: 1.32(6H,s), 2.04(1H,t), 2.47(2H,d).

IR (liquid film) 3300, 3000–2500, 1720 cm$^-$.

Step 3

The preparation of 2-chloro-4-(2',2'-dimethyl-pent-4-ynamido)-N,N-dimethylbenzamide.

2,2-Dimethylpent-4-ynoic acid was stirred in dry ether (15 ml) at room temperature while oxalyl chloride (1.53 g) in dry ether (5 ml) was added dropwise with stirring. After completion of the addition the mixture was stirred for ½ hour.

The mixture was decanted and the ether evaporated to give the acid chloride (0.417 g) as a pale liquid which was used without further purification.

To a stirred solution in methylene chloride of 4-amino-2-chloro-N,N-dimethylbenzamide (0.524 g) and triethylamine (0.534 g) was added 2,2-dimethylpent-4-ynoic carboxylic acid chloride (0.417 g) at 0°–5° C. After stirring for 1½ hours, the reaction mixture was washed with dilute hydrochloric acid, aqueous sodium bicarbonate and water. The methylene chloride solution was dried and evaporated to give a foam which crystallised to give the desired product as a pale orange solid (0.606 g), m.p. 154°–5° C.

NMR (CDCl$_3$, 270 MHz) δ: 1.40(6H,s), 2.17(1H,t), 2.52(2H,d), 2.87(3H,s), 3.13(3H,s), 7.05(1H,d), 7.33(1H,dd), 7.64(1H,d).

The following are examples of compositions suitable for agricultural and horticultural purposes which can be formulated from the compounds of the invention. Such compositions form another aspect of the invention. Percentages are by weight.

EXAMPLE 13

An emulsifiable concentrate is made up by mixing and stirring the ingredients until all are dissolved.

| Compound No. 1 of Table 1 | 10% |
|---|---|
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 14

The active ingredient is dissolved in methylene dichloride and the resultant liquid sprayed on to the granules of attapulgite clay. The solvent is then allowed to evaporate to produce a granular composition.

| Compound No. 2 of Table 1 | 5% |
|---|---|
| Attapulgite granules | 95% |

EXAMPLE 15

A composition suitable for use as a seed dressing is prepared by grinding and mixing the three ingredients.

| Compound No. 3 of Table 1 | 50% |
|---|---|
| Mineral oil | 2% |
| China clay | 48% |

EXAMPLE 16

A dustable powder is prepared by grinding and mixing the active ingredient with talc.

| Compound No. 4 of Table 1 | 5% |
|---|---|
| Talc | 95% |

EXAMPLE 17

A suspension concentrate is prepared by ball milling the ingredients to form an aqueous suspension of the ground mixture with water.

| Compound No. 5 of Table 1 | 40% |
|---|---|
| Sodium lignosulphonate | 10% |
| Bentonite clay | 1% |
| Water | 49% |

This formulation can be used as a spray by diluting into water or applied directly to seed.

EXAMPLE 18

A wettable powder formulation is made by mixing together and grinding the ingredients until all are thoroughly mixed.

| Compound No. 6 of Table 1 | 25% |
|---|---|
| Sodium lauryl sulphate | 2% |
| Sodium lignosulphonate | 5% |
| Silica | 25% |
| China clay | 43% |

EXAMPLE 19

The compounds were tested against a variety of foliar fungal diseases of plants. The technique employed was as follows.

The plants were grown in John Innes Potting Compost (No. 1 or 2) in 4cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace-5% of disease on untreated plants
2 = 6-25% of disease on untreated plants
1 = 26-59% of disease on untreated plants
0 = 60-100% of disease untreated plants The results are shown in Tables IV, V and VI.

TABLE IV

| Compound No. (Table I) | Puccinia Recondita (Wheat) | Erysiphe Graminis (Barley) | Venturia Inaequalis (Apples) | Cercospora Arachidicola (Peanut) | Plasmopara Viticola (Vines) | Phytophthora Infestans (Tomatoes) |
|---|---|---|---|---|---|---|
| 1 | 2 | 0 | 0 | 0 | 4 | 3 |
| 2 | 2 | 0 | 1 | 0 | 4 | 4 |
| 3 | 0 | 0 | 0 | 0 | 0 | 4 |
| 4 | 3 | 1 | 4 | — | 4 | 3 |
| 5 | 4 | 0 | 4 | 2 | 4 | 4 |
| 6 | 3 | 2 | 4 | 0 | 4 | 2 |
| 7 | 3 | 4 | — | 0 | 3 | 0 |
| 8 | 2 | 0 | 4 | 4 | 3 | 1 |
| 9 | 0 | 0 | 0 | 1 | 4 | 1 |
| 10 | 0 | 0 | 0 | 0 | 4 | 4 |
| 11 | 0 | 0 | 3 | 0 | 4 | 4 |

TABLE IV-continued

| Compound No. (Table I) | Puccinia Recondita (Wheat) | Erysiphe Graminis (Barley) | Venturia Inaequalis (Apples) | Cercospora Arachidicola (Peanut) | Plasmopara Viticola (Vines) | Phytophthora Infestans (Tomatoes) |
|---|---|---|---|---|---|---|
| 12 | 0 | 0 | 0 | 0 | 4 | 4 |
| 13 | 4 | 1 | — | — | 4 | 4 |
| 14 | 4 | 0 | — | 0 | 4 | 4 |
| 15 | 3 | 0 | — | 1 | 4 | 4 |
| 16 | 0 | 0 | 0 | 0 | 4 | 4 |
| 17 | 0 | 0 | 4 | 2 | 4 | 4 |
| 18 | 0 | 2 | 0 | 0 | 4 | 4 |
| 19 | 0 | 2 | 0 | 0 | 4 | 4 |
| 20 | 0 | 0 | 0 | 0 | 4 | 4 |
| 21 | 0 | 0 | 2 | 0 | 4 | 4 |
| 22 | 0 | 0 | 0 | 0 | 0 | 3 |
| 23 | 2 | 0 | 0 | 0 | 4 | 2 |
| 24 | 4 | 1 | 3 | — | 4 | 4 |
| 25 | 0 | 1 | 4 | 0 | — | 3 |
| 26 | 0 | 0 | 0 | 3 | 4 | 3 |
| 27 | 0 | 0 | 0 | 2 | 4 | 0 |
| 28 | 0 | 0 | 0 | 3 | 4 | 0 |
| 29 | 3 | 0 | 4 | 0 | 4 | 4 |
| 30 | 2 | 0 | 0 | 2 | 4 | 4 |
| 31 | 0 | 0 | 0 | 0 | 4 | 4 |
| 32 | 1 | 0 | 2 | 0 | 3 | 4 |
| 33 | 2 | 1 | 4 | 0 | 4 | 4 |
| 34 | 0 | 0 | 0 | 3 | 4 | 4 |
| 35 | 0 | 0 | 4 | 3 | 4 | 3 |
| 36 | 0 | 3 | 0 | 0 | 3 | 0 |
| 37 | 0 | 0 | 4 | 0 | 4 | 0 |
| 38 | 0 | 0 | 0 | — | 4 | 4 |
| 40 | 0 | 0 | 2 | — | 3 | 3 |
| 66 | 0 | 0 | 0 | — | 4 | 4 |
| 67 | 0 | 0 | 0 | 0 | 3 | 3 |
| 68 | 3 | 2 | — | 3 | 3 | 3 |

TABLE V

| Compound No. (Table II) | Puccinia Recondita (Wheat) | Erysiphe Graminis (Barley) | Venturia Inaequalis (Apples) | Cercospora Arachidicola (Peanut) | Plasmopara Viticola (Vines) | Phytophthora Infestans (Tomatoes) |
|---|---|---|---|---|---|---|
| 1 | 0 | 0 | 0 | 0 | 0 | 4 |
| 2 | 0 | 1 | 0 | 0 | — | 4 |
| 3 | 0 | 0 | 0 | 0 | 4 | 3 |
| 4 | 0 | 0 | 0 | 0 | 4 | 4 |
| 5 | 0 | — | 0 | — | 4 | 4 |
| 6 | 0 | 0 | 0 | 2 | 3 | 0 |
| 7 | 0 | 0 | 0 | — | 4 | 3 |

TABLE VI

| Compound No. (Table II) | Puccinia Recondita (Wheat) | Erysiphe Graminis (Barley) | Venturia Inaequalis (Apples) | Cercospora Arachidicola (Peanut) | Plasmopara Viticola (Vines) | Phytophthora Infestans (Tomatoes) |
|---|---|---|---|---|---|---|
| 1 | 2 | 0 | — | — | 4 | 0 |
| 3 | 2 | 2 | — | — | 4 | 0 |

We claim:

1. A compound of the formula (I):

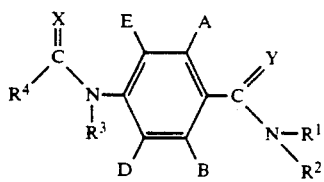

(I)

in which A and B are independently H, fluoro, chloro, bromo, $C_{1-4}$ alkyl, $C_{1-4}$ alkoxy or halo($C_{1-14}$)alkyl provided that both are not H; D and E are independently H or fluoro; $R^1$ is $C_{1-4}$ alkyl or $C_{1-4}$ alkoxy; $R^2$ is $C_{1-4}$ alkyl or $C_{1-4}$ alkoxy; $R^3$ is H; $R^4$ is trichloromethyl, $C_{2-8}$ alkyl or $C_{2-8}$ alkyl substituted with halogen, $C_{1-8}$ alkoxy or $R'S(O)_n$ in which $R^1$ is $C_{1-4}$ alkyl, $C_{2-4}$ alkenyl or $C_{2-4}$ alkynyl and n is 0, 1 or 2, cyclopropyl or cyclopropyl substituted with halogen or $C_{1-4}$ alkyl, $C_{2-8}$ alkenyl, $C_{2-8}$ alkynyl or $C_{2-8}$ alkoxy; and X and Y are both oxygen.

2. A compound according to claim 1 in which A and B are independently H, fluoro, chloro or bromo provided that both are not H; D and E are both H; $R^1$ is $C_{1-4}$ alkyl; $R^2$ is $C_{1-4}$ alkyl or $C_{1-4}$ alkoxy; $R^3$ is hydrogen; $R^4$ is $C_{3-6}$ alkyl, $C_{3-6}$ alkyl substituted with halogen, methoxy, methylthio or methylsulphonyl, cyclopropyl, cyclopropyl substituted with methyl, $C_{3-6}$ alkenyl, $C_{3-6}$ alkynyl or $C_{1-4}$ alkoxy; and X and Y are both oxygen.

3. A compound according to claim 1 in which A is chloro; B, D and E are all H; $R^1$ is methyl or ethyl; $R^2$ is methyl or ethyl; $R^3$ is hydrogen; $R^4$ is $C_{3-4}$ alkyl or cyclopropyl; and X and Y are both oxygen.

4. A compound according to claim 1 in which A is chloro; B, D and E are all H; $R^1$ and $R^2$ are independently methyl or ethyl; $R^3$ is hydrogen; $R^4$ is iso-propyl, t-butyl or cyclopropyl; and X and Y are both oxygen.

5. A compound of the formula (I.1):

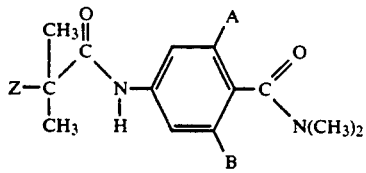
(I.1)

in which A is chloro, bromo or methyl; B is H, chloro, bromo or methyl; and Z is fluoro, chloro, bromo, methyl, ethyl or methoxy.

6. A compound according to claim 5 in which A is chloro, bromo or methyl and B is H, or A and B are both chloro or both methyl.

7. A compound according to claim 5 in which A is chloro or bromo and B is H, or A and B are both chloro; and Z is methyl.

8. A fungicidal composition comprising a fungicidally effective amount of a compound according to claim 1 and a fungicidally acceptable carrier or diluent therefor.

9. A compound according to claim 1 wherein $R^1$ is H, $C_{1-4}$ alkyl or $C_{1-4}$ alkoxy; $R^2$ is $C_{1-4}$ alkyl, $C_{1-4}$ alkoxy or optionally substituted phenyl; $R^4$ is trichloromethyl, $C_{2-8}$ alkyl optionally substituted with halogen, $C_{1-8}$ alkoxy or $R'S(O)_n$ in which $R'$ is $C_{1-4}$ alkyl, $C_{2-4}$ alkenyl or $C_{2-4}$ alkynyl and n is 0, 1 or 2, cyclopropyl optionally substituted with halogen or $C_{1-4}$ alkyl, $C_{2-8}$ alkenyl, $C_{2-8}$ alkynyl or $C_{2-8}$ alkoxy; and X and Y are oxygen.

10. A compound according to claim 1 wherein A is chlorine; B, D and E are hydrogen; Y and X are both oxygen; $R^1$ and $R^2$ are both methyl; $R^3$ is hydrogen and $R^4$ is $-C(CH_3)_2F$.

* * * * *